US 6,540,703 B1

(12) United States Patent
Lerman (10) Patent No.: US 6,540,703 B1
(45) Date of Patent: Apr. 1, 2003

(54) POST-OPERATIVE HIP ABDUCTION ORTHOSIS (76) Inventor: Max Lerman, 1950 Carla Ridge, Beverly Hills, CA (US) 90210

( * ) Notice: Subject to any disclaimer, the term of this patent is extended or adjusted under 35 U.S.C. 154(b) by 140 days.

(21) Appl. No.: 09/716,581

(22) Filed: Nov. 20, 2000

(51) Int. Cl.⁷ .................................................. A61F 5/00
(52) U.S. Cl. ................................ 602/5; 602/16; 602/19
(58) Field of Search .............................. 602/5, 16, 18, 602/19, 23, 26; 128/882

(56) References Cited

U.S. PATENT DOCUMENTS

| | | | | | |
|---|---|---|---|---|---|
| 4,481,941 A | * | 11/1984 | Rolfes | .......................... | 128/88 |
| 4,531,515 A | * | 7/1985 | Rolfes | ................... | 602/16 XZ |
| 4,905,678 A | * | 3/1990 | Cumins | ................ | 602/16 XZ |
| 6,039,707 A | * | 3/2000 | Crawford | ............... | 602/19 XZ |

* cited by examiner

Primary Examiner—Michael A. Brown
(74) Attorney, Agent, or Firm—Christie, Parker & Hale, LLP (57) ABSTRACT A post-operative hip abduction orthosis for preventing hip dislocation during recovery of a patient includes a pelvic support, a thigh cuff that fits around the upper thigh of the patient, and an upright adjustable hip support brace secured to the outside of the pelvic support and thigh cuff. The hip support brace extends alongside the hip joint and carries an adjustable hinge aligned with the hip joint of the patient. Hip brace adjustments control hip abduction and limit range of motion in hip rotation. Brace adjustments include laterally rotational and longitudinal alignment connections between upper and lower brace arms and the pelvic support and thigh cuff, respectively. The lower brace arm is angled outwardly relative to the upper brace arm to hold the patient's upper leg at a pre-set abduction angle. A silicone skin adhesion system on the inside of the pelvic support and thigh cuff prevents rotation and proximal/distal migration of the orthosis on the body of the patient.

23 Claims, 7 Drawing Sheets

POST-OPERATIVE HIP ABDUCTION ORTHOSIS

FIELD OF THE INVENTION

This invention relates generally to hip braces, and more particularly, to a hip brace worn temporarily after surgery to prevent dislocation of the hip from activities occurring during the healing process.

BACKGROUND OF THE INVENTION

Various hip surgery techniques are used for repairing or replacing bone structures in the pelvic and upper thigh regions of the human anatomy. Such surgery normally requires an incision of the muscle and tendon tissue adjacent to the pelvis such that the bone structure surrounded by such tissue may be accessed for replacement or repair. The muscle and tendon tissue not only facilitates movement of the skeletal hip structure but also assists in holding the thigh bone within the pelvic socket.

During recovery, the muscle and tendon tissue will be weakened and not completely effective in retaining the thigh bone within the pelvic socket. Accordingly, in some cases patients recovering from hip surgery inadvertently move the thigh and dislocate the femur from the pelvic socket. Certain movements of the thigh will not cause dislocation, and thus the patient should not be completely immobilized in those circumstances, to allow some minimal exercise of the healing muscles and tendons during the very early stages of the recovery process and to accommodate some mobility by the patient. Thigh movements commonly known to cause dislocation of the femur are the exaggerated flexion of the hip, such as pivoting the thigh forwardly toward the chest, or abduction of the thigh toward the other leg, or a combination of flexion and abduction such as crossing one leg over the other. In addition to causing an extreme amount of pain to the patient, hip dislocation may require the surgeon to reoperate to put the thigh bone back into the pelvic socket.

A hip abduction orthosis is a standard treatment to prevent recurrent hip dislocation. All hip orthoses control hip abduction and limit hip range of motion. Rotational control without extending the hip orthosis to the foot is not known to be available today. The present invention provides a hip orthosis which controls the motions mentioned and additionally controls hip rotation without extending the brace to the foot.

In the past certain braces have been used post-operatively to hold the patient's legs in a fixed position while the patient rests in bed for a few weeks after surgery. The patient must carefully observe certain precautions about hip movement that are to be avoided, as explained by a doctor, but in some instances these braces allow the hip to inadvertently become dislocated. Consequently, more rigid hip braces were developed to prevent hip dislocation. Prior rigid hip braces used after surgery include a long, rigid hinged bar at the side of the hip with a rotating angular limiter at the hip joint that confines angular rotation of the hip to a pre-set angle. A problem with such braces is that they are heavy, bulky, and expensive to manufacture. Another prior post-operative hip brace includes a waist belt connected to a thigh belt by flexible inelastic posterior straps, a medial strap, and anterior straps. Because the straps which connect the waist and thigh belts are flexible, this hip brace is unable to provide rigid support for patients recuperating from total hip replacement surgery.

Consequently, a need exists for a hip brace that is light weight, is not bulky, is inexpensive to manufacture, and can be applied to a patient post-operatively, to prevent hip abduction, hyperflexion, and twisting of the hip joint during recovery of the patient.

SUMMARY OF THE INVENTION

Briefly, one embodiment of the present invention comprises a post-operative hip abduction orthosis for preventing hip dislocation during recovery of a patient. The orthosis includes a pelvic support adjustably positionable around the pelvic region of the patient, a thigh cuff adjustably positionable around the upper thigh region of the patient and spaced apart below the pelvic support, and a vertically extending hip supporting brace connected between the pelvic support and the thigh cuff. The brace extends across the thigh region of the patient and comprises an elongated rigid upper arm secured to a side of the pelvic support above the hip joint and an elongated rigid lower arm secured to a side of the thigh cuff below the hip joint. The upper and lower brace arms extend toward the hip joint and are pivotally connected to each other to provide a hinge about which the upper and lower brace arms rotate on an axis adapted generally for alignment with the hip joint of the patient. Adjustable stops control the angular range of motion between the rigid arms of the hip brace when rotated about the hinge axis. Axially adjustable connections between the upper and lower brace arms and the pelvic support and thigh cuff, respectively, are used to adjust the vertical spacing between the pelvic support and the thigh cuff. A laterally rotatable attachment between the pelvic support and the upper brace arm is used for releasably adjusting and rigidly setting the rotational position of the upper brace arm on the pelvic support, independently of the axial alignment between the upper brace arm and the pelvic support. The rotational adjustment allows the hip joint to be rotated internally or externally.

In another embodiment, skin adhesion layers on the pelvic support and the thigh cuff prevent rotation of the orthosis during patient movements and/or when adjusting the position of the orthosis on the patient.

These and other aspects of the invention will be more fully understood by referring to the following detailed description and the accompanying drawings.

DETAILED DESCRIPTION

Figure 1:
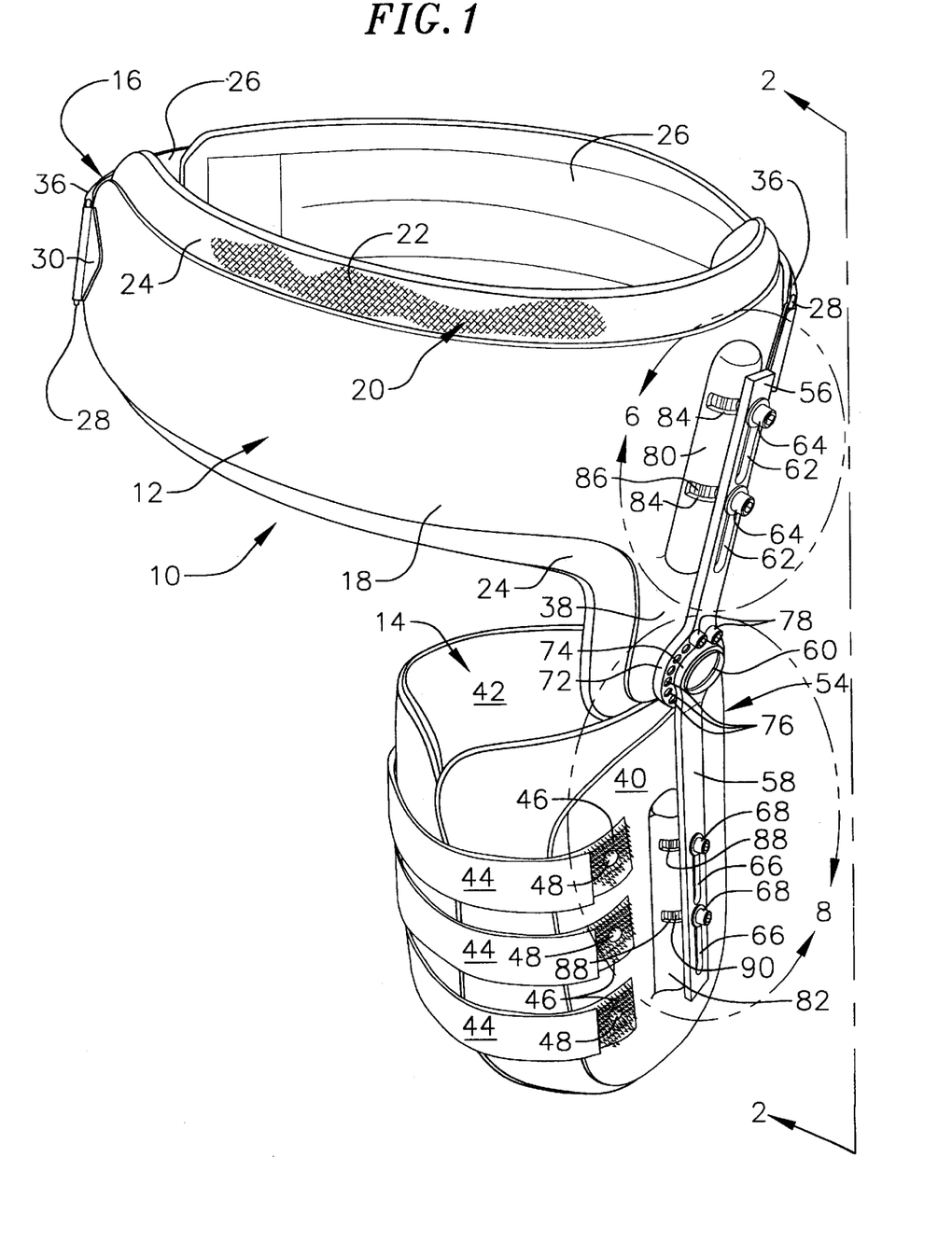
FIG. 1 is a perspective view showing a hip abduction orthosis according to principles of this invention.
Figure 2:
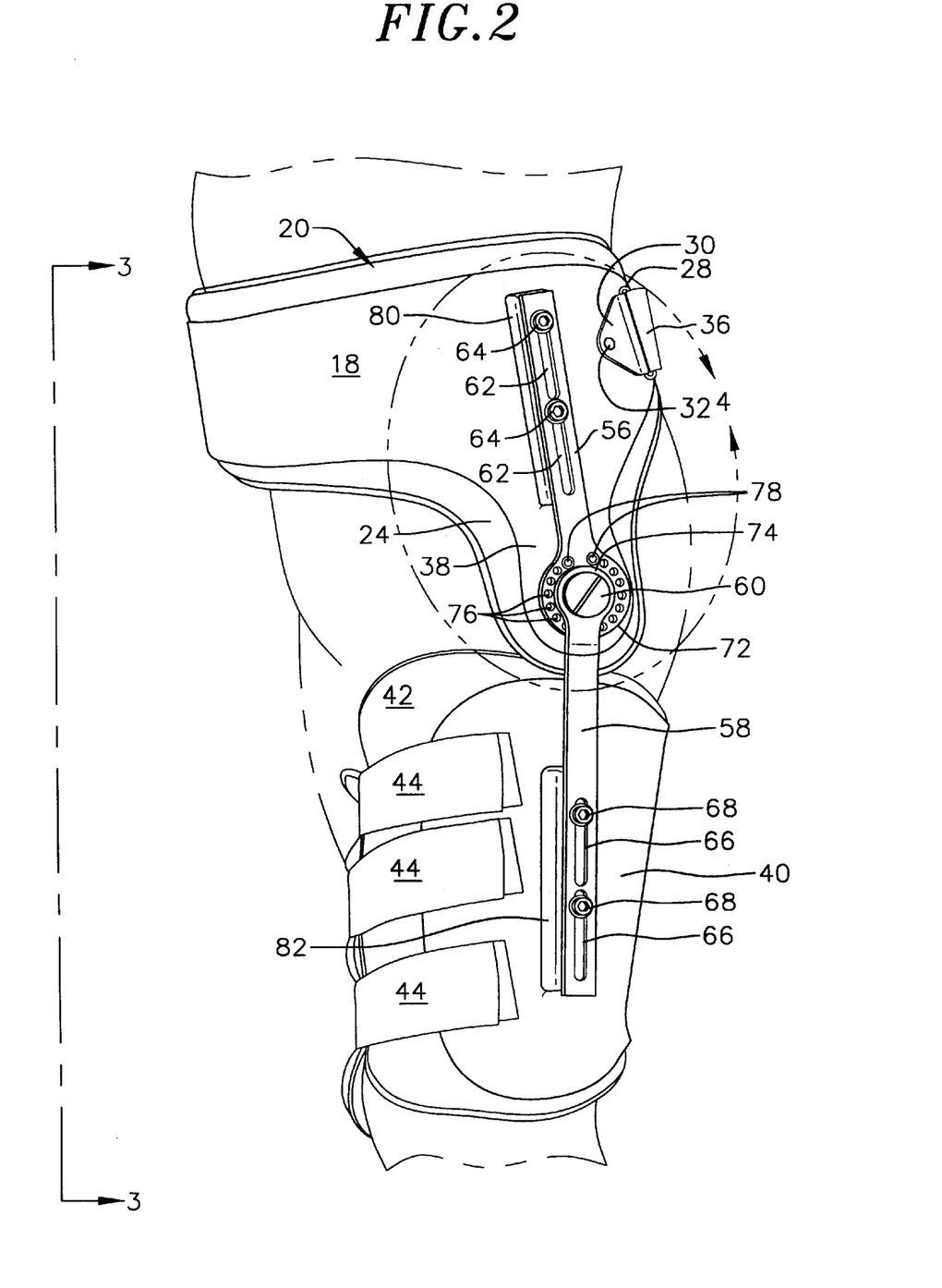
FIG. 2 is a side elevational view taken on line 2—2 of FIG. 1.
Figure 3:
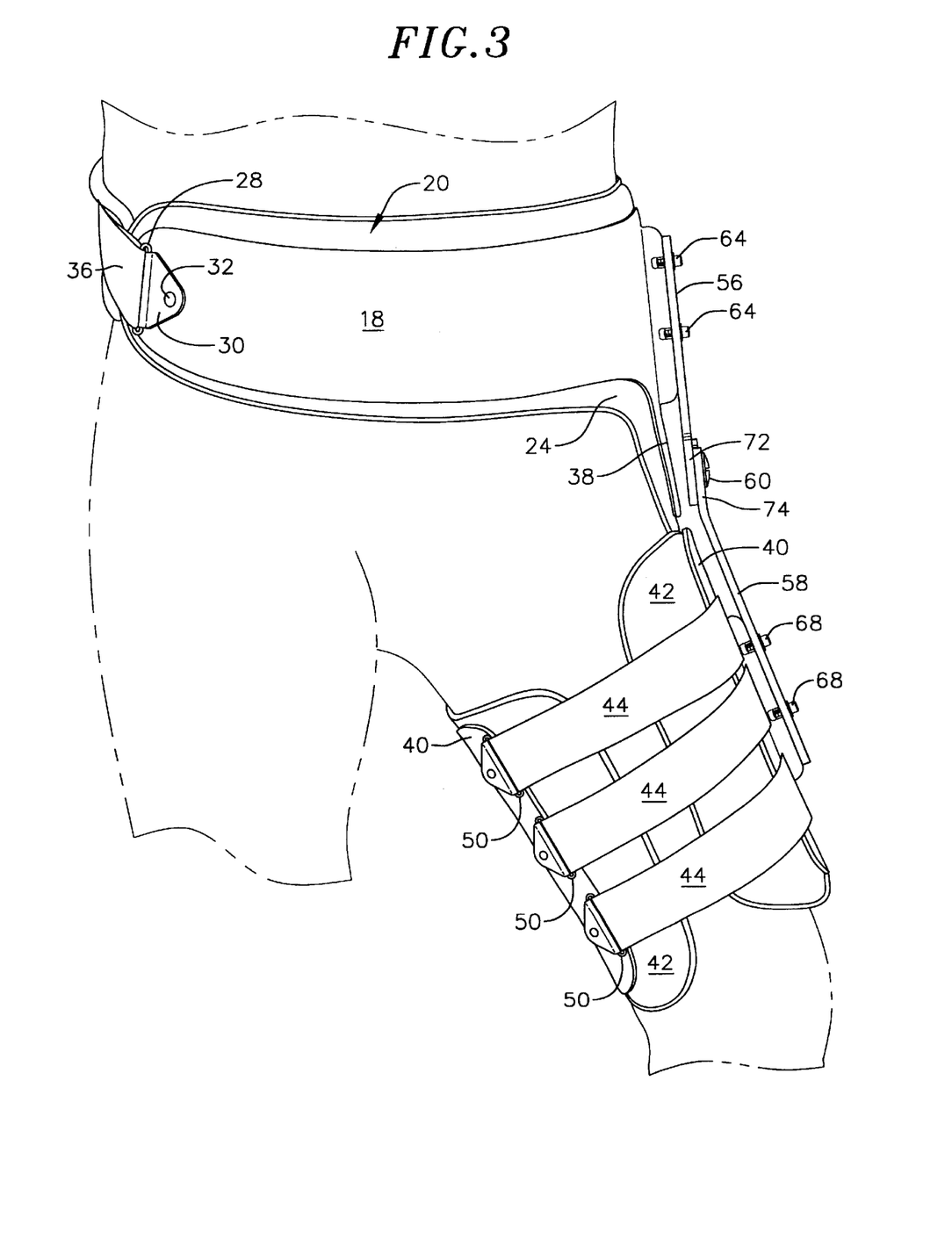
FIG. 3 is an elevational view taken on line 3—3 of FIG. 2.

Referring to FIGS. 1 through 3, a post-operative hip abduction brace 10 according to principles of this invention includes an elongated flexible pelvic support 12 and an elongated flexible thigh cuff 14 spaced vertically apart and extending generally parallel to each other. The pelvic support includes an adjustable flexible fastener system 16 on the rear half of the support for securing the pelvic support around the pelvic region of the patient (shown in phantom lines). Preferably, the supporting portion of the pelvic support comprises a generally U-shaped, semi-rigid, bendable front pelvic support member 18 which, in use, overlies the front pelvic region of the patient. The pelvic support member preferably is made from a lightweight bendable plastic material of sufficient thickness to provide support for adjustable components of the orthosis, as described below. The preferred plastic material is polyethylene or polypropylene, preferably about ⅜ to about ¼ inch thick. The width of the pelvic support member is about 3–½ inches. The pelvic support member is of sufficient length to extend around the front half of the patient's pelvic region. A layer 20 of padding is affixed to the inside face of the pelvic support member to overlie the pelvic region of the patient on the inside of the pelvic support member. The padding is preferably made from a resilient relatively thick compressible plastic film material 22, such as polyurethane foam, with a thin flexible outer layer 24 of a soft material, such as velour.

The fastener system 16 on the rear half of the pelvic support includes an elongated flexible rear strap 26 made from a soft lightweight material such as polyester. Each end of the flexible rear strap is affixed to a corresponding end of pelvic support member, preferably by a corresponding ring fastener 28 secured to a flexible bracket 30, which in turn is affixed to the pelvic support by a corresponding pivot pin 32. An elongated layer of a flexible friction fastener material 34, preferably the pile or velour type, such as that sold under trademark Velcro, is fastened to the rear outside face of the rear strap. This fastener extends most of the length of the flexible rear strap. Separate elongated flexible strips 36 of a cooperating friction fastener material, such as the hook type sold under the trademark Velcro, are secured to the outer ends of the rear strap 24. During use, these flexible friction fastener strips 36 are threaded through the ring fasteners at the ends of the front pelvic support and then folded back on themselves to overlie and releasably fasten to the cooperating layer of friction fastener material on the rear side of the pelvic support. Thus, one friction fastener strip can be affixed to a ring fastener at one end of the pelvic support while the other free end of the rear strap can be adjusted to fit around the patient's pelvic region and then releasably fastened after the adjustment by securing the friction fastener at that end to the corresponding ring fastener on the pelvic support.

A downwardly projecting region 38 of the pelvic support extends toward the thigh cuff, on a side where the orthosis is supported by the adjustable brace described below. This downwardly projecting region of the pelvic support generally overlies the hip region of the patient during use. The padding 24 on the inside of the pelvic support also protrudes downwardly and overlies this region 38 of the support.

The thigh cuff of the orthosis comprises a flexible semi-rigid bendable thigh support member 40 adapted to extend around most of the patient's upper thigh region below the hip region being supported by the orthosis. The flexible thigh support 40 is preferably made from a bendable plastic material, such as polyethylene or polypropylene, similar to the pelvic support member 18. A layer of padding 42 is affixed to the inside face of the thigh support member similar to the padding on the upper pelvic support member.

A system of adjustable fasteners on the opposite ends of the thigh cuff releasably secure the thigh cuff firmly around the upper thigh of the patient. These fasteners preferably comprise separate elongated flexible strips 44, which include a hook-type friction fastener material 46, secured to one end of the cuff by pivot pins 48. The inside face of each strip comprises a cooperating friction fastener material of the pile or velour type. The opposite ends of the fastener strips are threaded through cooperating ring fasteners 50 on the opposite ends of the thigh cuff support member. The friction fasteners are then folded back on themselves and releasably fastened to the friction fastener regions on the inside of the friction fastener strips to adjustably fasten the thigh cuff around the patient's upper thigh.

A hinged orthotic brace 54 has a rigid upper brace arm 56 secured to a side of the pelvic support member above the protruding region of the pelvic support. The orthotic brace has a rigid lower brace arm 58 secured to a side of the thigh cuff below the protruding region of the pelvic support. The upper and lower brace arms extend toward each other along the sides of the patient's hip region during use, toward a central pivot 60 where the inner ends of the brace arms are rotatably secured to each other to form a hinge. A pair of narrow elongated slotted openings 62 are spaced apart along the length of the upper brace arm. The openings receive a corresponding pair of upper fasteners 64 for rigidly but releasably securing the upper brace arm to a side of the pelvic support. Similarly, a pair of narrow elongated slotted openings 66 are spaced apart along the length of the lower brace arm. These openings receive a corresponding pair of lower fasteners 68 for rigidly but releasably securing the lower brace arm to the side of the thigh cuff.

Detailed construction of the brace 54 and its attachments to the pelvic support and thigh cuff are best understood by referring to FIGS. 4 through 9.

Figure 4:
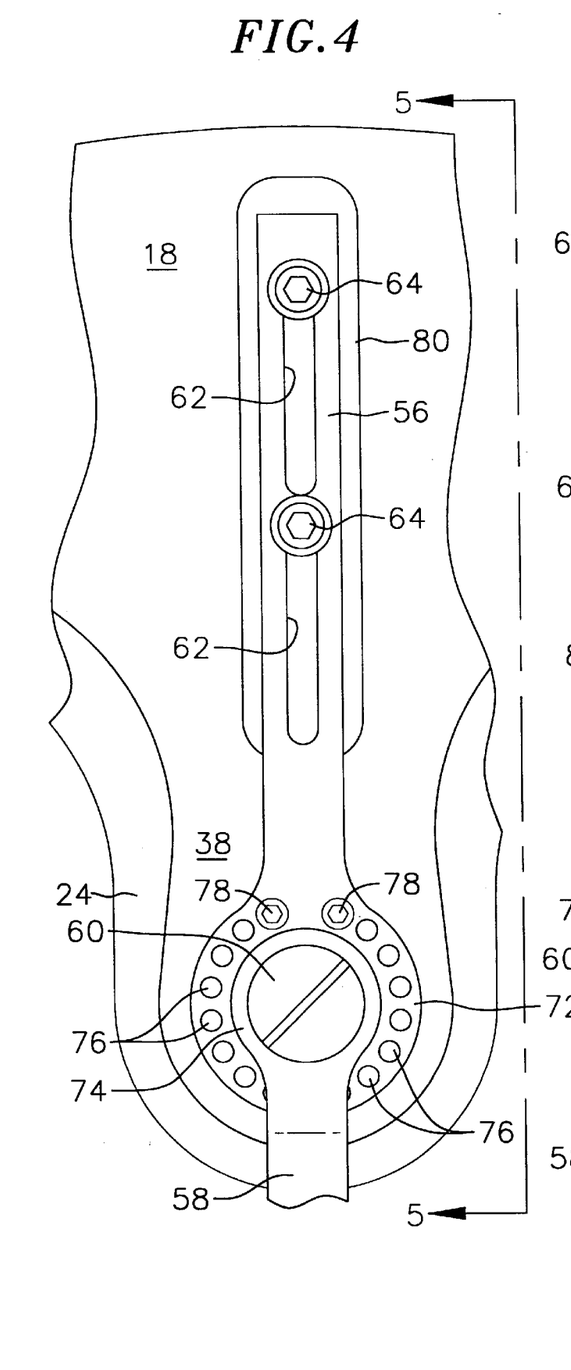
FIG. 4 is an enlarged fragmentary elevational view taken within the circle 4 of FIG. 2.
Figure 5:
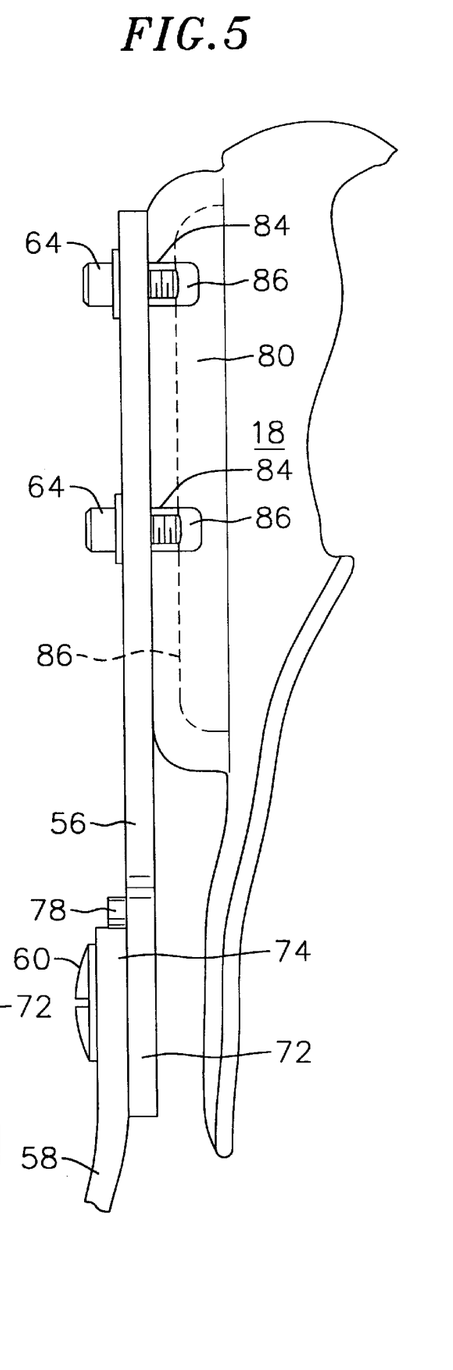
FIG. 5 is a fragmentary side elevational view taken on line 5—5 of FIG. 4.

The hinged portion of the brace 54 includes an enlarged lower end portion 70 of the upper brace arm and an enlarged upper portion 72 of the lower brace arm. These enlarged regions of the brace arms overlie each other at the pivot axis of the brace. The pivot 60 comprises a rotatable pivot pin shaft (not shown) which extends through the overlying enlarged regions of the brace members. The pivot pin provides a rotatable hinge axis about which the brace arms are rotatable while aligned with the hip joint during use. The enlarged lower portion 72 of the upper brace arm is larger in diameter than the overlying enlarged upper portion of the lower brace arm. This forms an annular base around the pivot pin 60 that carries a series of threaded openings 76 circumferentially spaced apart around the outside of the pivot pin. Separate threaded stop pins 78 are inserted into selected openings 76 on opposite sides of the pivot pin. During use, the stop pins provide a means for controlling the angular range of motion of the lower brace arm relative to the upper brace arm.

The upper and lower brace arms each have axially adjustable and rotatably adjustable means of attachment to the pelvic support and thigh cuff, respectively. The fasteners 64 on the upper brace arm are releasable for allowing the upper brace arm to slide axially to a desired position with respect to its attachment to the pelvic support. This allows the pelvic support to be moved toward or away from the pivot axis of the hinge to a desired position, followed by tightening the upper fasteners 64 for making the axial adjustment. Similarly, the fasteners 68 in the lower brace arm are releasable for allowing the lower brace arm to slide axially to a desired position with respect to its attachment to the thigh cuff. This allows the thigh cuff to be moved toward or away from the pivot axis of the hinge to a desired position followed by tightening the lower fasteners 68.

Rotational adjustment of the upper brace arm relative to the pelvic support is provided by mounting the inside of the upper brace arm on a circularly curved bearing surface of a reinforced outwardly projecting elongated mounting ridge 80 molded into the pelvic support in alignment with the upper brace arm. This ridge is long and narrow and in alignment with the upper brace arm. In cross-section, the mounting ridge is shaped as a semi-circle, facing toward the underside of the upper brace arm, with its circularly curved outer bearing surface contacting and supporting the upper brace arm.

Similarly, rotatable adjustment of the lower brace arm relative to the thigh cuff is provided by mounting the inside of the lower brace arm on a circularly curved surface of a reinforced outwardly projecting elongated mounting ridge 82 molded into the thigh cuff in alignment with the lower brace arm. This ridge is also long and narrow and in alignment with the lower brace arm. In cross-section the lower ridge is shaped as a semi-circle facing toward the inside of the lower brace arm.

Figure 6:
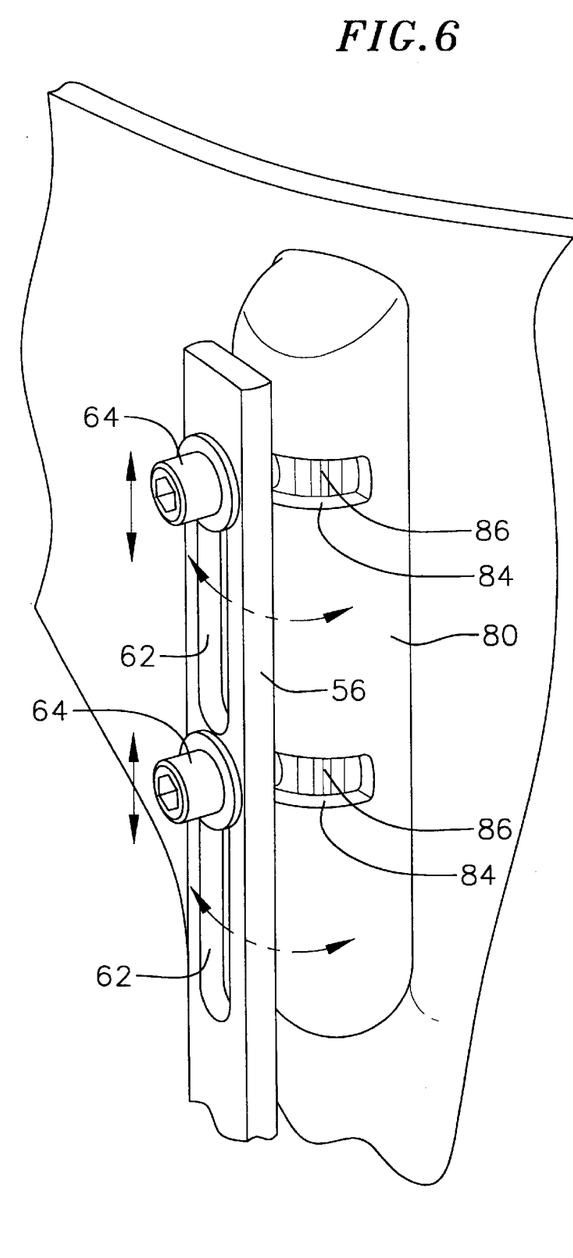
FIG. 6 is a fragmentary enlarged perspective view taken within the circle 6 of FIG. 1.
Figure 7:
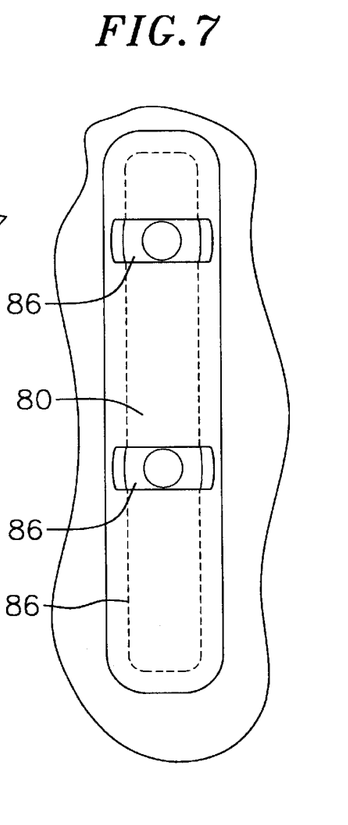
FIG. 7 is an elevational view showing a portion of the connector shown in FIG. 6.

The upper ridge 80 includes a pair of spaced apart parallel slotted openings 84 in alignment with corresponding upper fasteners 64. These slotted openings extend laterally across the rounded surface of the ridge 80 in alignment with each of the upper fasteners. On the inside of the ridge, an elongated metal reinforcing bar 86 is inserted into the void space within the ridge. This reinforcing bar has a semi-circular cross-section and is shaped to match the interior configuration of the ridge. The reinforcing bar is also free to rotate within the ridge. The upper fasteners extend through the slotted openings 84 and into corresponding threaded openings in the reinforcing bar. By loosening the upper fasteners, the upper brace arm is able to rotate in the direction of the slotted openings maintaining contact with the circular bearing surface of the ridge. This allows the brace arm to be rotated laterally to a desired position on the ridge followed by tightening the upper fasteners to secure the rotational adjustment of the upper brace arm relative to the pelvic support.

Figure 8:
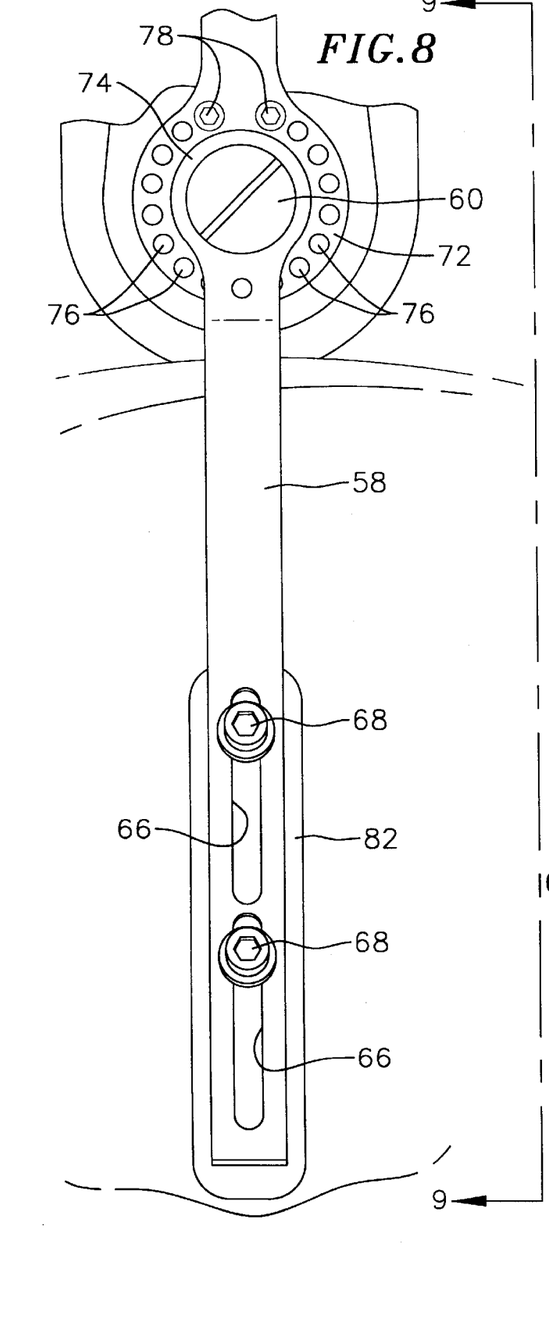
FIG. 8 is an enlarged fragmentary elevational view taken within the circle 8 of FIG. 1.
Figure 9:
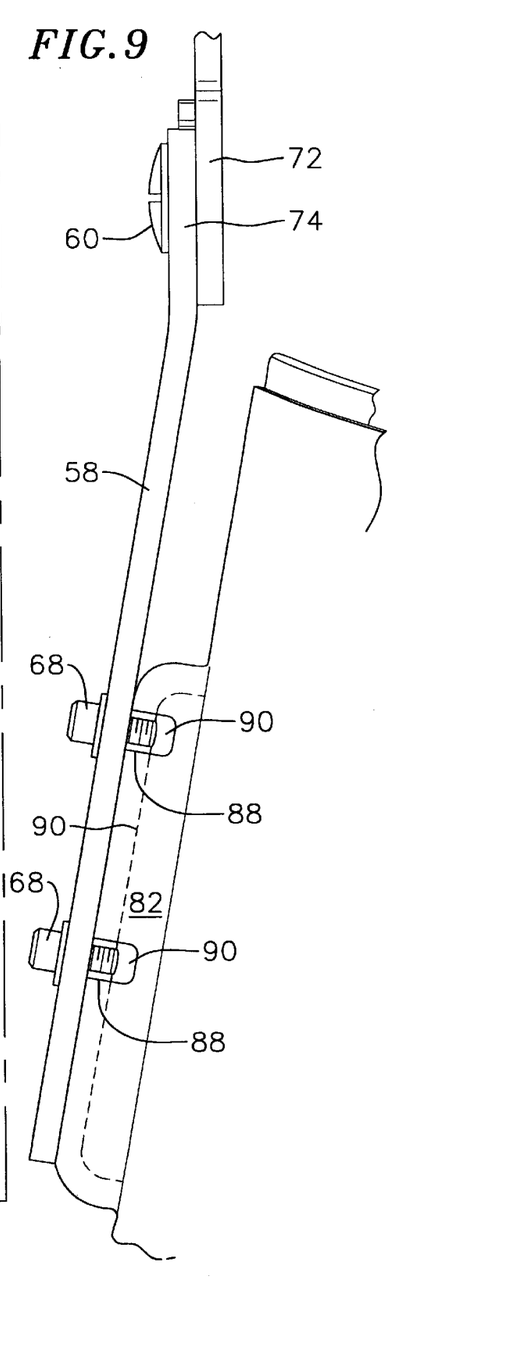
FIG. 9 is an enlarged fragmentary elevational view taken on line 9—9 of FIG. 8.

Similarly, the lower ridge 82 includes a pair of spaced apart parallel slotted openings 88 in alignment with corresponding lower fasteners 68. These slotted openings extend laterally across the rounded surface of the lower ridge in alignment with each of the upper fasteners. On the inside of the lower ridge, an elongated metal reinforcing bar 90 is inserted into the void space within the ridge. This reinforcing bar has a semi-circular cross-section and is shaped to match the interior configuration of the lower ridge. The reinforcing bar is also free to rotate within the ridge. The lower fasteners extend through the slotted openings 88 and into corresponding threaded openings in the lower reinforcing base. By loosening the lower fasteners, the lower bar arm is able to rotate in the direction of the slotted openings 88 to a desired lateral rotational position on the lower ridge. The lower fasteners are then tightened to secure the rotational alignment of the lower brace arm relative to the thigh cuff.

As shown best in FIG. 3, the lower brace arm 58 is angled laterally outwardly relative to the axis of the upper brace arm 56. The lower brace arm is straight for essentially its entire length starting from the hinge area and angling laterally outwardly at about a 10°–20° angle relative to the axis of the upper brace arm. During use, the fasteners 68 are tightened to hold the lower brace arm in a rigid position supporting the thigh cuff. This securely holds the upper thigh at a fixed abduction angle relative to the other leg.

The rotational adjustment of the upper brace arm 56 on the upper bearing surface 80 provides a means for rotating the upper portion of the brace to a desired set rotational position (to bring the patient's toe out for example). The fastener 64 on the upper brace arm 56 are loosened to allow the upper brace arm to rotate in the direction of the arrows shown in FIG. 6. The fasteners on the upper brace arm slide laterally along the slotted openings on the half-round bearing surface 80 to adjust the lateral rotational position of the upper brace arm on the pelvic support. The upper fasteners are then tightened to hold the brace in its set rotational position. Similarly, the fasteners 68 on the lower brace arm can be loosened and a corresponding lateral rotational adjustment can be made by moving the lower brace arm to a corresponding rotational position on the half-round lower bearing surface 82 prior to tightening the fasteners 68.

Figure 10:
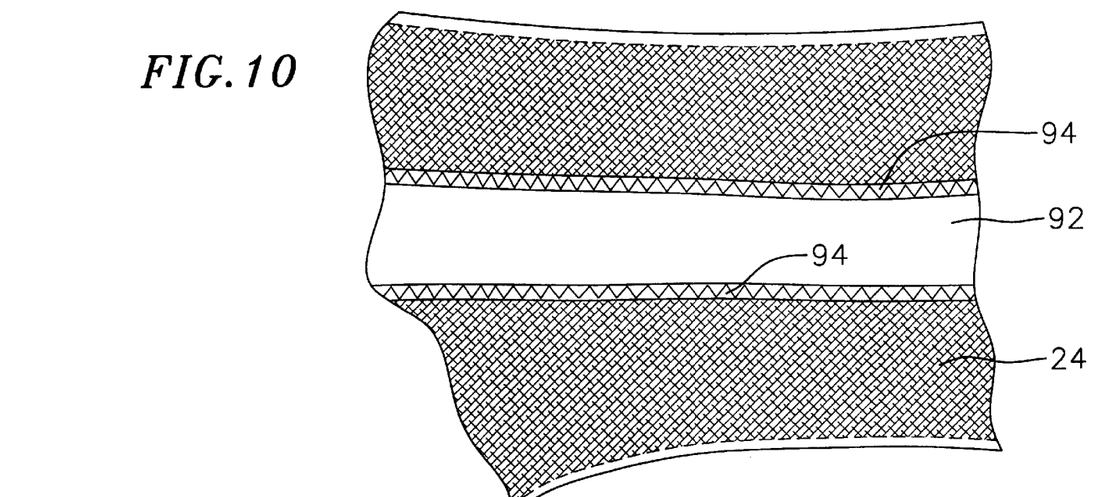
FIG. 10 is a fragmentary semi-schematic elevational view showing a skin adhesion system on the inside of a pelvic support.
Figure 11:
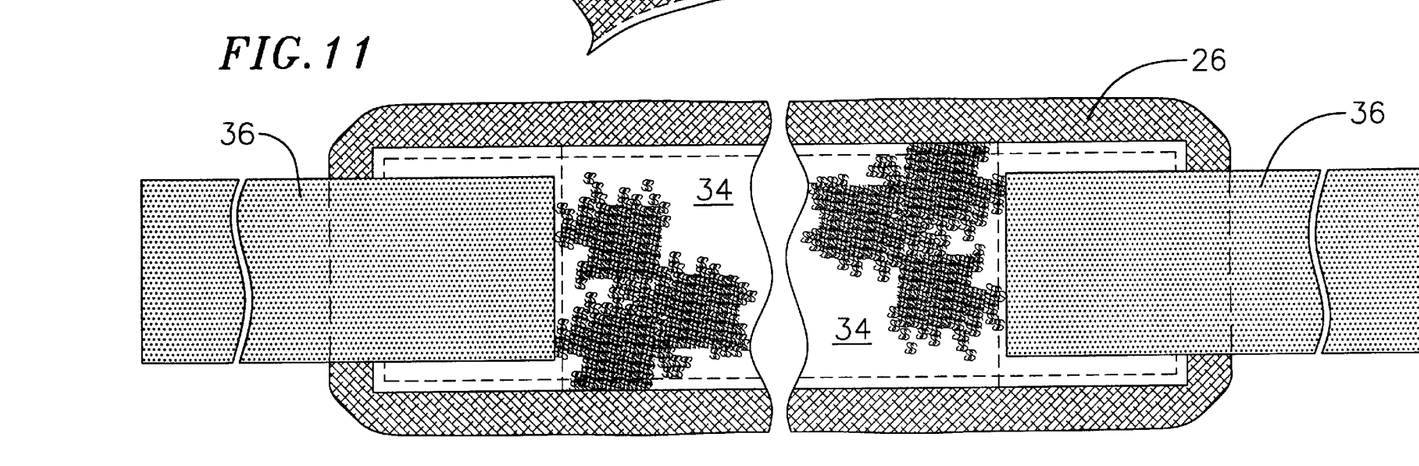
FIG. 11 is an enlarged fragmentary semi-schematic elevational view showing the outside of the pelvic support.

FIGS. 10 and 11 illustrate a non-skid skin adhesion layer secured to the pelvic support to enhance frictional contact between the brace and the patient's skin or clothing. The inside face of the pelvic support has an elongated skin adhesion layer 92 extending for essentially the entire length of the support (see FIG. 10). This skin adhesion layer is affixed by peripheral stitching 94 to the inside of the padding 20 which covers the inside surface of the pelvic support. The skin adhesion layer preferably comprises a layer of non-skid material capable of frictionally adhering to but easily removable from contact with the patient's skin for long periods of time without detrimental effects to the patient's skin or comfort during use. The skin adhesion layer is preferably made by a layer of thermoplastic silicone gel or similar medical grade material having a somewhat tacky surface for providing frictional contact with the skin when held in tight contact with it. The skin adhesion material is an inert material which can be worn against the skin for long periods of time without causing skin irritations or discomfort. The presently preferred material is a silicone gel such as Walco Silicone V-1082 HiPro Clear available as a gel mixed with a promoter and/or a tri-block polymer with medical grade mineral oil by Silipos. The finished layer of skin adhesion material can be secured to a nylon strip and then fastened along its length to the inside face of the pelvic support. Alternatively, the gel can be poured onto a flexible layer of a reinforcing fabric such as Tricot, nylon or other similar flexible fabric material, such as a woven fibrous material which can absorb the gel material and maintain it as a thin layer of uniform thickness on its surface. In the embodiment in which the gel layer is reinforced by a nylon strip it has a tensile strength greatly exceeding that of the film of gel material itself which is wrapped around the reinforcing layer. The reinforcing layer avoid tearing or more easily fastens the gel material to the inside of the pelvic support.

A similar layer of a non-skid material is secured to the padded made surface of the thigh cuff.

During use, the pelvic support is fitted around the anterior side of the patient, and when the patient is reclined, there is no pressure on the back or spine. The skin adhesion layer which contacts the skin or clothing prevents rotation and proximal/distal migration on the body. The rotational adjustment of the brace on the side of the pelvic support allows the hip joint to be rotated externally or internally. The skin adhesion layer on the thigh cuff controls rotation or proximal/distal migration, and the rotational adjustment allows the thigh/leg to be rotated externally or internally to a properly set rotational position. The hinged brace which attaches to the pelvic support and thigh cuff allows the rotational adjustment. The half-round metal bar which reinforces the half-round bearing surface locks the brace to the pelvic support and thigh cuff. The rotational adjustments on the pelvic support and thigh cuff prevent the contacted areas of the patient from rotating while making the brace position adjustments.

I claim:

1. A post-operative hip abduction orthosis for preventing hip dislocation during recovery of a patient, comprising:

a pelvic support adjustably positionable around the pelvic region of the patient;

a thigh cuff adjustably positionable around the upper thigh region of the patient and spaced below the pelvic support; and a vertically extending hip supporting brace connected between the pelvic support and the thigh cuff to extend across the thigh region of the patient, the hip supporting brace comprising an elongated rigid upper arm secured to a side of the pelvic support above the hip joint of the patient, and an elongated rigid lower arm secured to a side of the thigh cuff below the hip joint of the patient, the upper and lower brace arms extending toward the hip joint of the patient and pivotally connected to each other remote from their points of attachment to the pelvic support and thigh cuff to provide a hinge about which the upper and lower brace arms rotate on an axis adapted generally for alignment with the hip joint of the patient; the hip supporting brace further comprising adjustable stops for controlling the angular range of motion between the arms of the hip brace when the brace arms are rotated about the hinge axis, axially adjustable connections between the upper and lower brace arms and the pelvic support and thigh cuff, respectively, for use in adjusting the vertical spacing between the pelvic support and the thigh cuff, and a laterally rotatable attachment between the pelvic support and the upper brace arm for use in releasably adjusting and rigidly setting the rotational position of the upper brace arm on the pelvic support independently of the axial alignment between the upper brace arm and the pelvic support.

2. Apparatus according to claim 1 including a releasable attachment of the pelvic support to the upper brace arm which includes a bearing surface projecting outwardly from the pelvic support and on which the upper brace arm is releasably secured for rotating the upper brace arm point of attachment laterally on the bearing surface to adjust its rotational position.

3. Apparatus according to claim 2 in which the bearing surface is a rounded surface extending laterally across the side of the pelvic support.

4. Apparatus according to claim 3 in which the bearing surface is elongated along the length of the pelvic support generally in alignment with the length of the upper brace arm, and in which the axial adjustment of the upper brace arm also is affixed to the bearing surface.

5. Apparatus according to claim 4 in which the bearing surface comprises an elongated half-round projection reinforced internally by a rigid bar into which fasteners are releasably secured for rigidly fastening the upper brace arm to the bearing surface.

6. Apparatus according to claim 1 further including a laterally rotatable attachment between the lower brace arm and the thigh cuff for releasably adjusting and rigidly setting the rotational position of the lower brace arm on the thigh cuff, independently of the axial alignment between the lower brace arm and the thigh cuff.

7. Apparatus according to claim 6 including a releasable attachment of the lower brace arm to the thigh cuff which includes a bearing surface projecting outwardly from the thigh cuff and on which the lower brace arm is releasably secured for rotating the lower brace arm point of attachment laterally on the bearing surface to adjust its rotational position.

8. Apparatus according to claim 7 in which the bearing surface is a rounded surface extending laterally across the side of the thigh cuff.

9. Apparatus according to claim 8 in which the bearing surface is elongated along the length of the thigh cuff generally in alignment with the length of the lower brace arm, and in which the axial adjustment of the lower brace arm also is affixed to the bearing surface.

10. Apparatus according to claim 9 in which the bearing surface on the thigh cuff comprises an elongated half-round projection reinforced internally by a rigid bar into which fasteners are releasably secured for fastening the lower brace arm to the bearing surface.

11. Apparatus according to claim 1 in which the lower brace arm extends laterally outwardly at an angle relative to the upper brace arm to provide a fixed abduction angle when the thigh cuff is affixed to the thigh region of the patient.

12. Apparatus according to claim 1 in which the inside of the pelvic support comprises a layer of non-skid material.

13. Apparatus according to claim 12 in which the non-skid layer is secured to a flexible reinforcing strip having a substantially greater tensile strength than the skin adhesion layer.

14. Apparatus according to claim 13 in which the non-skid layer is made from a silicone gel material or a medical grade tri-block polymer.

15. Apparatus according to claim 12 in which the inside of the thigh cuff has a layer of non-skid material.

16. Apparatus according to claim 15 in which the non-skid layer on the thigh cuff is secured to a flexible reinforcing strip having a substantially greater tensile strength than the corresponding skin adhesion layer.

17. Apparatus according to claim 16 in which the non-skid layer on the thigh cuff is made from a silicone gel material or a medical grade tri-block polymer.

18. A post-operative hip abduction orthosis for preventing hip dislocation during recovery of a patient, comprising:

a pelvic support adjustably positionable around the pelvic region of the patient;

a thigh cuff adjustably positionable around the upper thigh region of the patient and spaced below the pelvic support;

a vertically extending hip supporting brace connected between the pelvic support and the thigh cuff to extend across the thigh region of the patient, the hip supporting brace comprising an elongated rigid upper arm secured to a side of the pelvic support above the hip joint of the patient, and an elongated rigid lower arm secured to a side of the thigh cuff below the hip joint of the patient, the upper and lower brace arms extending toward the hip joint of the patient and pivotally connected to each other remote from their points of attachment to the pelvic support and thigh cuff to provide a hinge about which the upper and lower brace arms rotate on an axis adapted generally for alignment with the hip joint of the patient; the hip supporting brace further comprising adjustable stops for controlling the angular range of motion between the arms of the hip brace when the brace arms are rotated about the hinge axis, axially adjustable connections between the upper and lower brace arms and the pelvic support and thigh cuff, respectively, for adjusting the vertical spacing between the pelvic support and the thigh cuff;

a layer of a non-skid material on the inside of the pelvic support for functionally securing the pelvic support to the pelvic region of the patient to prevent rotation of the pelvic support;

a layer of non-skid material on the inside of the thigh cuff for functionally securing the thigh cuff to the upper thigh region of the patient to prevent rotation of the thigh cuff;

a laterally rotatable attachment between the pelvic support and the upper brace arm for use in releasably adjusting and rigidly setting the rotational position of the upper brace arm on the pelvic support independently of the axial alignment between the upper brace arm and the pelvic support; and a laterally rotatable attachment between the lower brace arm and the thigh cuff for releasably adjusting and rigidly setting the rotational position of the lower brace arm on the thigh cuff independently of the axial alignment between the lower brace arm and the thigh cuff.

19. A post-operative hip abduction orthosis for preventing hip dislocation during recovery of a patient, comprising:

a pelvic support adjustably positionable around the pelvic region of the patient;

a thigh cuff adjustably positionable around the upper thigh region of the patient and spaced apart below the pelvic support;

a vertically extending hip supporting brace connected between the pelvic support and the thigh cuff to extend across the thigh region of the patient, the hip supporting brace comprising an elongated rigid upper arm secured to a side of the pelvic support above the hip joint of the patient, and an elongated rigid lower arm secured to a side of the thigh cuff below the hip joint of the patient, the upper and lower brace arms extending toward the hip joint of the patient and pivotally connected to each other remote from their points of attachment to the pelvic support and thigh cuff to provide a hinge about which the upper and lower brace arms rotate on an axis adapted generally for alignment with the hip joint of the patient; the hip supporting brace further comprising adjustable stops for controlling the angular range of motion between the arms of the hip brace when the brace arms are rotated about the hinged axis, axially adjustable connections between the upper and lower brace arms and the pelvic support and thigh cuff, respectively, for use in adjusting the vertical spacing between the pelvic support and the thigh cuff, and a laterally rotatable attachment between the pelvic support and the upper brace arm for use in releasably adjusting and rigidly setting the rotational position of the upper brace arm on the pelvic support independently of the axial alignment between the upper brace arm and the pelvic support; and in which the lower brace arm extends laterally outwardly at an angle relative to the upper brace arm to provide a fixed abduction angle when the thigh cuff is secured to the thigh region of the patient.

20. A post-operative hip abduction orthosis for preventing hip dislocation during recovery of a patient, comprising:

a pelvic support adjustably positionable around the pelvic region of the patient;

a thigh cuff adjustably positionable around the upper thigh region of the patient and spaced below the pelvic support;

a vertically extending hip supporting brace connected between the pelvic support and the thigh cuff to extend across the thigh region of the patient, the hip supporting brace comprising an elongated rigid upper arm secured to a side of the pelvic support above the hip joint of the patient, and an elongated rigid lower arm secured to a side of the thigh cuff below the hip joint of the patient, the upper and lower brace arms extending toward the hip joint of the patient and pivotally connected to each other remote from their points of attachment to the pelvic support and thigh cuff to provide a hinge about which the upper and lower brace arms rotate on an axis adapted generally for alignment with the hip joint of the patient; the hip supporting brace further comprising adjustable stops for controlling the angular range of motion between the arms of the hip brace when the brace arms are rotated about the hinge axis, axially adjustable connections between the upper and lower brace arms and the pelvic support and thigh cuff, respectively, for use in adjusting the vertical spacing between the pelvic support and the thigh cuff, and a laterally rotatable attachment between the pelvic support and the upper brace arm for use in releasably adjusting and rigidly setting the rotational position of the pelvic support relative to the upper brace arm independently of the axial alignment between the pelvic support and upper brace arm;

in which the outer walls of the pelvic support and thigh cuff are each made from a semi-rigid, bendable polymeric material, and the brace arm connections to the pelvic support and thigh cuff comprise outwardly projecting regions molded in the pelvic support and thigh cuff outer walls, each reinforced internally by a rigid bar to hold corresponding fasteners.

21. A post-operative hip abduction orthosis for preventing hip dislocation during recovery of a patient, comprising:

a pelvic support adjustably positionable around the pelvic region of the patient;

a thigh cuff adjustably positionable around the upper thigh region of the patient and spaced below the pelvic support;

a vertically extending hip supporting brace connected between the pelvic support and the thigh cuff to extend across the thigh region of the patient, the hip supporting brace comprising an elongated rigid upper arm secured to a side of the pelvic support above the hip joint of the patient, and an elongated rigid lower arm secured to a side of the thigh cuff below the hip joint of the patient, the upper and lower brace arms extending toward the hip joint of the patient and pivotally connected to each other remote from their points of attachment to the pelvic support and thigh cuff to provide a hinge about which the upper and lower brace arms rotate on an axis adapted generally for alignment with the hip joint of the patient;

the hip supporting brace having a controllable angular range of motion between the arms of the hip brace when the brace arms are rotated about the hinge axis;

axially adjustable connections between the upper and lower brace arms and the pelvic support and thigh cuff, respectively, for use in adjusting the vertical spacing between the pelvic support and the thigh cuff;

a laterally rotatable attachment between the pelvic support and the upper brace arm for use in releasably adjusting and rigidly setting the rotational position of the upper brace arm on the pelvic support; and a laterally rotatable attachment between the lower brace arm and the thigh cuff for releasably adjusting and rigidly setting the rotational position of the lower brace arm on the thigh cuff.

22. Apparatus according to claim 21 including a releasable attachment of the pelvic support to the upper brace arm which includes an upper bearing surface projecting outwardly from the pelvic support and on which the upper brace arm is releasably secured for rotating the upper brace arm point of attachment laterally on the upper bearing surface to adjust its rotational position; and a releasable attachment of the lower brace arm to the thigh cuff which includes a lower bearing surface projecting outwardly from the thigh cuff and on which the lower brace arm is releasably secured for rotating the lower brace arm point of attachment laterally on the lower bearing surface to adjust its rotational position.

23. Apparatus according to claim 22 in which the upper bearing surface comprises an elongated half-round projection reinforced internally by a rigid bar into which fasteners are releasably secured for rigidly fastening the upper brace arm to the upper bearing surface; and in which the lower bearing surface on the thigh cuff comprises an elongated half-round projection reinforced internally by a rigid bar into which fasteners are releasably secured for fastening the lower brace arm to the lower bearing surface.

* * * * *